(12) United States Patent
Komatsu et al.

(10) Patent No.: US 11,930,810 B2
(45) Date of Patent: Mar. 19, 2024

(54) CRYOPRESERVATION CONTAINER

(71) Applicant: 77 KC CO., LTD., Kanagawa (JP)

(72) Inventors: Hirohide Komatsu, Kanagawa (JP); Tsutomu Sawa, Kanagawa (JP)

(73) Assignee: 77KC Co., Ltd., Kanagawa (JP)

( * ) Notice: Subject to any disclaimer, the term of this patent is extended or adjusted under 35 U.S.C. 154(b) by 1167 days.

(21) Appl. No.: 16/332,709

(22) PCT Filed: Sep. 12, 2017

(86) PCT No.: PCT/JP2017/032944
§ 371 (c)(1),
(2) Date: Jun. 24, 2019

(87) PCT Pub. No.: WO2018/051993
PCT Pub. Date: Mar. 22, 2018

(65) Prior Publication Data
US 2019/0297877 A1   Oct. 3, 2019

(30) Foreign Application Priority Data

Sep. 13, 2016   (JP) .................................. 2016-179044

(51) Int. Cl.
*A01N 1/02*     (2006.01)
*A61B 17/43*    (2006.01)
(Continued)

(52) U.S. Cl.
CPC ............. *A01N 1/0268* (2013.01); *A01N 1/02* (2013.01); *A61B 17/43* (2013.01); *A61B 17/435* (2013.01);
(Continued)

(58) Field of Classification Search
CPC ...... A01N 1/0268; A01N 1/02; A01N 1/0252; A61B 17/43; A61B 17/435; A61D 19/02;
(Continued)

(56) References Cited

U.S. PATENT DOCUMENTS 5,777,303 A * 7/1998 Berney ................. B01L 3/5453
                                                        235/487
8,872,627 B2 * 10/2014 Davidowitz ............ B01L 3/508
                                                        206/459.5
(Continued)

FOREIGN PATENT DOCUMENTS

JP    2007066011 A    3/2007
JP    2014212724 A    11/2014
(Continued)

OTHER PUBLICATIONS

English Machine Translation of JP2014212724 A (see attached NPL_JP2014212724_EnglishTranslation.pdf) (Year: 2014).*
(Continued)

*Primary Examiner* — Sunita Reddy
(74) *Attorney, Agent, or Firm* — SoCal IP Law Group LLP; Angelo J. Gaz

(57) ABSTRACT

Provided is a cryopreservation container that prevents confusion of specimens to be used for treatment and that is suitable for individual management of fertilized eggs and the like to be cryopreserved. IC tags are attached to a cryopreservation tank 61, a canister 51, a cane 41, and cryopreservation containers such as an ovum storage container 1 and sperm storage containers 71, 81. The cryopreservation containers may also have individual identification codes attached hereto. An ovum storage container 11 is configured by fitting an IC tag 12 from the rear end of a rod-like part 2 of a conventional ovum storage container 1. In addition, the IC tag 12 is formed by providing an inlet 15 inside a thin-walled pipe 14 made of a synthetic resin. The inlet 15 may be fixed at both ends by means of fixing members 18, 18 composed of a nonconductive material, or may be integrally molded with a nonconductive synthetic resin material 20.

16 Claims, 22 Drawing Sheets

(51) Int. Cl.
*A61B 17/435* (2006.01)
*A61D 19/02* (2006.01)
*A61J 3/00* (2006.01)
*C12M 1/24* (2006.01)
*G06K 19/077* (2006.01)

(52) U.S. Cl.
CPC ........... *A61D 19/02* (2013.01); *A61D 19/024* (2013.01); *A61J 3/00* (2013.01); *C12M 1/24* (2013.01); *G06K 19/077* (2013.01); *G06K 19/07758* (2013.01)

(58) Field of Classification Search
CPC ....... A61D 19/024; A61D 19/022; A61J 3/00; A61J 2200/44; C12M 1/24; C12M 23/06; G06K 19/077; G06K 19/07758; G06K 19/0773; G06K 19/07786
USPC ....................................................... 435/303.1

See application file for complete search history.

(56) References Cited

U.S. PATENT DOCUMENTS

| | | | |
|---|---|---|---|
| 2010/0141384 A1* | 6/2010 | Chen | G06K 19/041 340/10.1 |
| 2013/0027185 A1* | 1/2013 | Lavi | B01L 9/06 340/10.1 |
| 2015/0379390 A1* | 12/2015 | Morris | G06K 19/07758 235/492 |
| 2016/0358062 A1* | 12/2016 | Morris | G06K 19/041 |
| 2019/0000073 A1* | 1/2019 | Pedersen | A01N 1/0268 |

FOREIGN PATENT DOCUMENTS

| | | |
|---|---|---|
| WO | 2007077996 A1 | 7/2007 |
| WO | 2018051993 A1 | 3/2018 |

OTHER PUBLICATIONS

World Intellectual Property Office, International Search Report for PCT Application No. PCT/JP2017/032944, dated Nov. 28, 2017, 3 total pages.

* cited by examiner (A)

(B)

(A)

(B)

(A)

(B)

(B)

(A)

(C)

(D)

(A)

(B)

(A)

(B)

(A)

(B)

CRYOPRESERVATION CONTAINER

RELATED APPLICATION INFORMATION

This patent claims priority from International PCT Patent Application No. PCT/JP2017/032944, filed Sep. 12, 2017 entitled, "CRYOPRESERVATION CONTAINER", which claims priority to Japanese Patent Application No. 2016-179044, filed Sep. 13, 2016 all of which are incorporated herein by reference in their entirety.

TECHNICAL FIELD

The present invention relates to a cryopreservation container used to cryopreserve reproductive cells such as sperms, ova or fertilized eggs of patients and reproductive cells such as sperms, ova or fertilized eggs of animals.

BACKGROUND ART

In recent years, as for infertility treatments, treatments such as in-vitro fertilization or microinsemination are executed widely. The number of in-vitro fertilization executed are increasing suddenly from about 2002. The resulting number of in-vitro fertilization executed was about 370,000 in 2013 and it is expected that the number of in-vitro fertilization executed will be more than 700,000 in 2020.

As for in-vitro fertilization, the number of ova which are operated in the first period of treatment is about 5 to 20, and ova of women and sperms of men are collected and then they are treated, fertilized, cultivated, stored, melted and transplanted. At that time, ova and sperms of each patient are distinguished exactly and should be treated, fertilized, cultivated, stored, melted and transplanted, and of course it is not forgiven that they are operated by mistake.

In recent years, technique to cryopreserve fertilized eggs (embryo) has improved and the pregnancy rate equivalent to fresh embryo is obtained as to frozen embryo and also a merit capable to set up transplant time to uterus flexibly is recognized. Therefore, the ratio of in-vitro fertilization using frozen embryo is increasing greatly.

The state in which an ovum fertilized is called a fertilized egg, and the fertilized egg is divided into 4 cells aged embryo after two days and is further divided, and then the embryo will be transplanted to uterus.

A method to freeze and store the embryo in the state of being ready to transplantation becomes the mainstream on infertility treatments at the present time.

At the time of cryopreserving, sperms are injected into a sperm preservation container such as a specimen tube, a straw and the like, and ova and fertilized eggs are preserved on a ovum preservation container such as a cryotop [Registered Trademark owned by Kitazato Supply Co. Ltd.] having a sheet portion, a cryoloop having a loop portion and the like.

Then the plural sperm preservation containers and the plural ovum preservation containers are maintained on a cane, the plural canes which maintain the plural sperm preservation containers and the like are maintained in a canister, and the plural canisters are stored in a tank for cryopreserving and preserved (see Patent Literatures 1 and 2).

Here, liquid nitrogen is filled up in the cryopreservation tank for cryopreserving and the subjects are cryopreserved under extreme lower temperature of −196° C. at an atmosphere of liquid phase or gas phase.

Conventionally, it was not allowed to cryopreserve unfertilized eggs to execute in-vitro fertilization in the future, but recently, various laws were revised to allow cryopreserving of unfertilized eggs for the said purpose. As the result, it is expected that cases in which unmarried women cryopreserve her own ova are increasing.

At the cryopreservation as mentioned above, conventionally, information data such as a specimen number, a patient name, a collected day and time and the like was written by one's hand on the end portion of a sperm preservation container, a ovum preservation container, a cane and the like, or labels on which the information mentioned were put on the end portion of. Then embryo cultivators recognize the written on part of the containers and instrument with his the cultivator's eyes or the information labels put on them with the cultivator's eyes so as to distinguish which patient's sperms or ova are in the container.

CITATION LIST

Patent Literature

Patent Literature 1: JP 2015-089396 A
Patent Literature 2: JP 2016-067807 A

SUMMARY OF INVENTION

Technical Problem

By the method as mentioned above in which information data such as a specimen number, a patient name, a collected day and time and the like was written by one's hand on the end portion of a sperm preservation container, a ovum preservation container, a cane and the like, or the method as mentioned above in which labels on which the information was mentioned were put on the end portion of them, embryo cultivators recognize the written point of the containers and instrument or the labels put on them with the cultivator's eyes, and therefore, there is a possibility that the case may occur of operating with specimen which is an object for treatment that is misidentified by mistake by the cultivator.

On the other hand, the plural sperm preservation containers, the plural ovum preservation containers and the plural canes are maintained in a canister, and the plural canisters are stored in a cryopreservation tank which is filled up with liquid nitrogen and preserved under the environment of −196° C. Therefore, when the containers and instruments are taken out from the cryopreservation tank, frost and the like adhere on them or on the label, unless the frost is stripped off or melted, embryo cultivators cannot recognize a specimen number and the like. As the result, it may take a long time for embryo cultivators to recognize a specimen number and the like so as to lower the working efficiency and the frost becomes a factor which causes embryo cultivators to operate a wrong specimen by human mistake.

Further, in the case that it takes a long time until embryo cultivators take off the sperm preservation containers, the ovum preservation containers and the canes from the cryopreservation tank and recognize a specimen number and the like on the containers, instrument or the label, sperms and fertilized eggs are placed under the normal temperature during the time, and the internal temperature of them increases and they are easy to change their nature. As the result, this becomes a factor to decrease the fertilization ratio and the implantation ratio.

Furthermore, conventionally, at the time that embryo cultivators execute the work such as collection, treatment, fertilization, cultivation, cryopreservation, melting, implantation and the like of ova and sperms, he enters the data in recording papers or the recording display of a personal computer and record the data. However, patients who were executed the treatment cannot know information in the progress of the treatment without the timing of consultation because the state of the treatment is not specified timely to the patients.

Furthermore, in the system in which a label printed with a barcode is used and the barcode is read by a barcode reader, when frost adheres the label, there occurs a problem that a barcode cannot be read.

Further, the width of the place where a label can be attached to is very narrow, therefore, it is necessary to attach the label to appropriate position carefully in order to read the barcode correctly and the work is troublesome.

The present invention has been made in order to resolve such problems as mentioned above, and it is an object of the present invention to provide a cryopreservation container which is suitable for individual management of reproductive cells such as sperms, ova, fertilized eggs and the like to be cryopreserved, and which prevents confusion of sperms, ova, fertilized eggs and the like which are objects of treatment, improves work efficiency of embryo cultivators greatly, controls decrease of fertilization ratio and implantation ratio, realizes the traceability (history tracing possibility) to record all working of treatment including working objects, working details, workers and working day and time, and further by which patients can know information in the progress of treatment easily.

Solution to Problem

In order to achieve the above object, a cryopreservation container of the present invention is characterized in that an IC tag is mounted thereon.

Further an individual identification code is attached.

The IC tag can work and can be preserved for a long term in liquid nitrogen atmosphere at −196° C.

The cryopreservation container is a cryopreservation tank, a canister, a cane, an ovum preservation container or a sperm preservation container.

The cryopreservation container is an ovum preservation container and an IC tag is fitted from the rear end of rod-like portion of a conventional ovum preservation container.

Here, an IC tag is screwed or engaged with the rear end of rod-like portion of a conventional ovum preservation container.

IC tag is included to a conventional ovum preservation container.

The IC tag is formed by providing an inlet inside a thin-walled pipe made of a synthetic resin.

An internal diameter of a middle part of the thin-walled pipe of the IC tag is a little smaller than a diameter of a circumscribed circle in the rod-like portion of the ovum preservation container.

ID connected to an identification code recorded in the IC tag is printed on or a label in which an ID is printed is attached to a surface of the thin-walled pipe of the IC tag.

Information of subject cryopreserved or an ID connected to its information is recorded in the IC tag.

Color information colored is also registered in the IC tag.

The cryopreservation container is a sperm preservation straw and an IC tag is put into an outside of a sealing part of a conventional sperm preservation straw and a sealing part is formed around the outside.

The cryopreservation container is a specimen tube and an IC tag is mounted in a leg portion of a body of a conventional specimen tube.

The cryopreservation container is a specimen tube and an IC tag is included in a leg portion of a body of a conventional specimen tube.

The cryopreservation container is a cane and an IC tag is inserted and mounted in a hooking portion of a body of a conventional cane.

The cryopreservation container according to descriptions herein, wherein the IC tag is formed by providing a tag case forming a frame-like portion fitted to a flex IC tag.

An ID connected to an identification code recorded in the IC tag is printed on or a label in which an ID is printed is attached to the surface of the IC tag.

Color information colored is also registered in the IC tag.

The cryopreservation container is a canister and an IC tag is suspended from a hooking portion of a conventional canister.

A cryopreservation tank number, canister number, a top and bottom of the canister and the like is registered in the IC tag.

Type code which can identify a kind of cryopreservation container is recorded in the IC tag.

The IC tag is sterilized by radiation, autoclave, plasma, gas or the like.

Advantageous Effects of Invention

According to the cryopreservation container of the invention, an embryo cultivator can read the information by an identification code/IC tag reader. Therefore, the confusion of specimens to be the subject of treatment does not occur by mistaking a specimen number and the like.

Further, in the case that a sperm preservation container, an ovum preservation container, a cane and the like are taken out from a cryopreservation tank, even if frost and the like are attached to the surface of them, information can be read by an identification code/IC tag reader. Therefore, ID, a specimen number and the like can be recognized without removing frost and the like, and working efficiency of the embryo cultivator can be greatly improved.

It takes a little time to take out a sperm preservation container, an ovum preservation container, a cane and the like from the cryopreservation tank and recognize ID, a specimen number and the like by the embryo cultivator, or else, it is not necessary to take out them from liquid nitrogen. Therefore, sperms, ova, and the like does not change in quality rarely in the working time, after all, the fertilization ratio and the implantation ratio can be imp roved greatly.

In the case that an embryo cultivator executes work of collection, treatment, fertilization, cultivation, preservation, implantation and the like of ova and sperms, he enters the information in the recording display of a personal computer and stores the information in the personal computer. Therefore, a patient can recognize the information in appropriate time by a portable phone and the like and thereby reliability of treatment can be improved.

As a result mentioned above, processing ability and working ability of an embryo cultivator become clear, effectivity of cultivation liquid depended on individual variation of fertilized eggs also become clear, and then, by improving the matter, pregnancy rate of infertility treatment can be expected to improve greatly.

DESCRIPTION OF EMBODIMENTS

Figure 1:
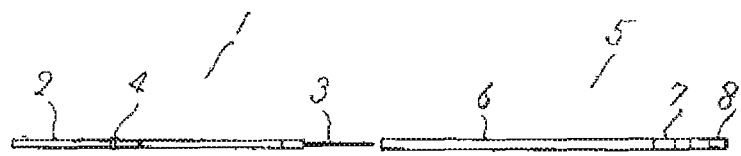
FIG. 1 is a front view of a conventional ovum preservation container.

In development of cryopreservation containers of the present invention, development of IC tag capable of working in liquid nitrogen of −196° C. for cryopreservation is the most important matter.

In the normal IC tag, the lower temperature range where the IC tag can work is until about −40° C., actually, reading can not be executed correctly at a temperature under −80° C.

In the invention, ability to read the IC tag mounted is needed without taking out a subject witch is preserved within liquid nitrogen.

As for an IC tag, electromagnetic wave of 13.56 MHz sent from an antenna of reader is received by a resonant circuit of 13.56 MHz comprising a coil of inlet and a capacitor of IC chip to be energy which operates an electric circuit inside.

The matter that the energy is more than the minimum electric power capable of operating the IC circuit is necessary condition for reading the IC tag.

As the result, for example, in the place where the energy is less than the minimum electric power when the reader antenna is moved far away from the IC tag, the IC tag does not work at all.

A parallel resonant circuit is formed by capacitance of a tuning circuit IC chip and inductance of a coil connected to the outside, the resonant frequency is expressed as follows:

$$f = \frac{1}{2\pi\sqrt{LC}} \quad \text{[formula 1]}$$

Further, Q (Quality Factor), which is a value showing sharpness of a peek in a series resonant circuit and affects performance of an IC tag greatly, is expressed as follow:

$$Q = \frac{1}{R}\sqrt{\frac{L}{C}} \quad \text{[formula 2]}$$

The formula shows that Q is larger as series resistance R in the tuning circuit is smaller, or as inductance L is larger. Accordingly, even if an IC tag is positioned in the same field of magnetic-flux density, energy transmitted is larger as Q is larger, and communication efficiency becomes improved.

Therefore, as for IC tag having a small external form, it is necessary to require large value of Q by taking measures such as reducing resistance by mean of making a wire diameter of an antenna coil as thick as possible, reducing distribution capacity and the like.

Further, as the dielectric constant of liquid nitrogen is 1.4, capacitance among coil wires in liquid nitrogen is larger than that in air. In order to reduce the change, it is efficient to fill up filler having a low dielectric constant around the coil to detach the distance from liquid nitrogen.

The capacitance between input terminals of an IC chip is configured by PN structure of a semiconductor inside. The capacity has a temperature characteristics and the capacitance has a trend to be reduced as the temperature is lower, though the temperature characteristics is different by species.

By the some parameters are cooperated together, the resonant frequency of IC tag in liquid nitrogen is about 0.1-0.3 MHz higher than that in normal temperature. Influence caused by the change of resonant frequency on the communication efficiency of a small IC tag is larger than that of a large IC tag, and therefore, delicate adjustment of resonant frequency is needed.

When temperature of IC chip is lowered until −196° C., the characteristics of IC circuit is changed, and then, the response wave is slowed down and it is difficult to read the IC tag.

In case that plural IC tags are existed, it is necessary to detect collision of signals by means of ant-collision method, the response wave is slowed down under the environment of −196° C., and then, it is difficult to judge and it takes long time to read.

Based on the consideration as mentioned above, at the time that IC tag capable of working under the environment of −196° C., some innovation are executed on the points as follows:
1. Resonant frequency in normal temperature is adjusted so as to amend the changing quantity of resonant frequency.
2. Design which heightens Q value by reducing a series resistance R is executed.
3. Configuration in which a coil of IC tag is not contact to liquid nitrogen directly is realized in order to prevent the change of capacitance among coil wires caused by that the dielectric constant of liquid nitrogen of 1.4 is larger than that of air.
4. Necessary parameters of IC chip capable of working under the environment of −196° C. are provided and IC chip suitable for the parameters is selected.

Preferred embodiments of a cryopreservation container of the present invention will be described in detail below with reference to the drawings.

Devices, instruments and implements used in cryopreservation are a cryopreservation tank, canisters, canes, specimen tubes, sperm preservation straws, ovum preservation containers, protection sleeves and like.

As shown in FIG. 1, a conventional ovum preservation container comprises a rod-like portion 2 of square pillar and a support plate 3 made of synthetic resin, and a guard portion 4 is formed in the middle portion of the rod-like portion 2.

On the other hand, a protection sleeve 5 comprises a thin-walled pipe 6 made of synthetic resin, and a cotton stopper 7 and a weight 8 are arranged in the near of the closed end.

And the fertilized egg is mounted on the tip end portion of the support plate 3 with a little preservation liquid, and is frozen suddenly in liquid nitrogen, and then the protection sleeve 5 is pushed on so as to tach the guard portion 4 and is covered on the support plate 3

Figure 2:
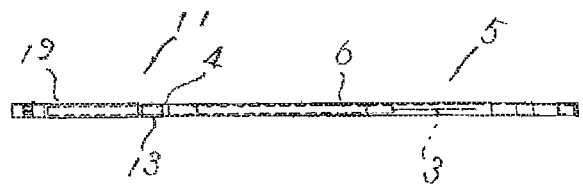
FIG. 2 (A) is a front view and (B) is an exploded view of one embodiment of an ovum preservation container of the present invention.
Figure 2:
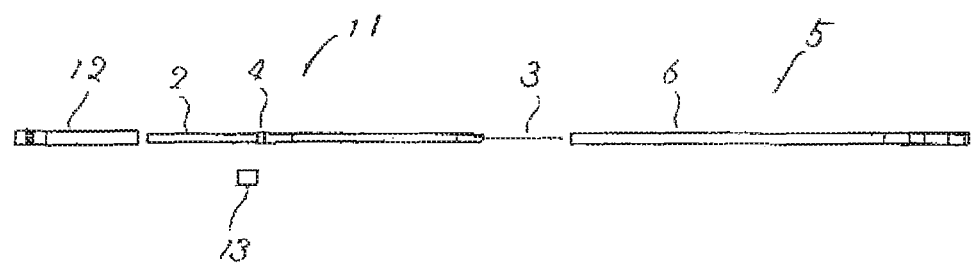

As shown in FIG. 2, an ovum preservation container 11 is configured by fitting in the IC tag 12 from the rear portion of the rod-like portion 2 of an ovum preservation container 1 and also winding the label 13 between the IC tag 12 and the guard portion 4.

The IC tag 12 of the invention comprises a thin-walled pipe 14 made of synthetic resin material and an inlet 15 inserted in the thin-walled pipe 14.

Figure 3:
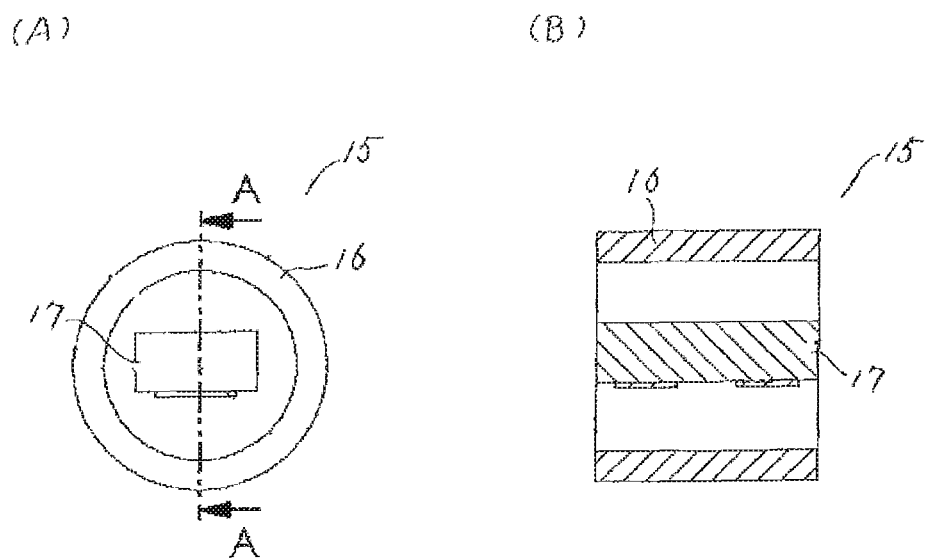
FIG. 3 (A) is a side view and (B) is a sectional view of one embodiment of an inlet of an IC tag.

As shown in FIG. 3, as the inlet 15, the inlet in which IC chip 17 is arranged inside the coil 16 wound in plural layers to be cylindrical shape can be adopted.

Figure 4:
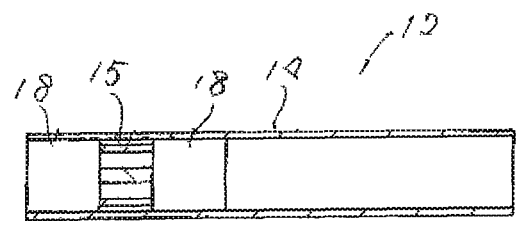
FIG. 4 is a sectional view of one embodiment of an IC tag of the ovum preservation container inserted the inlet shown in FIG. 3.

One embodiment of the IC tag 12 adopted an inlet 15, as shown in FIG. 4, comprises a thin-walled pipe 14 made of synthetic resin material, an inlet 15 inserted in the thin-walled pipe 14 and fixing members 18, 18 which fix the inlet 15 from both sides.

The fixing member 18, 18 is formed by shaping non-electric conductive material such as synthetic resin, rubber and the like, and synthetic resin material such as polypropylene, polyethylene and the like and elastic material such as silicon rubber, teflon [registered trademark of Kemars Co. Ltd.] rubber and the like can be adopted.

Further, an individual number of IC tag of itself (an individual number written in IC chip at the time of manufacture: UID) or an identification code connected to the individual number is printed on the surface of the IC tag, or else a label printed an individual number or an identification code is attached to the surface of the IC tag. The identification code is also recorded as related information at the time that IC tag is registered to the system.

Whereby, in the case that information of IC tag cannot be read owing to breakdown and so on, it is possible to read the information of IC tag from a data base using the identification code printed on the surface of IC tag or printed in the label. Further, in the case that IC tag is exchanged, it is possible to change the IC tag by transferring data to new IC tag.

Figure 5:
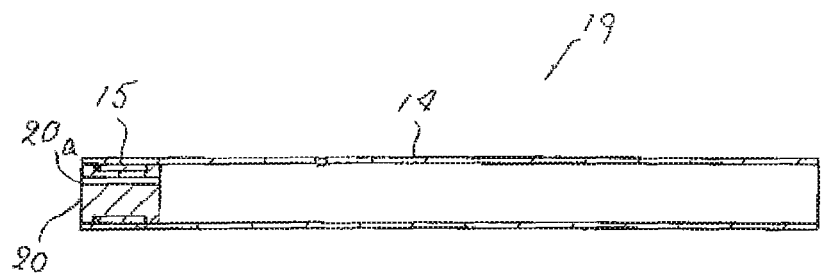
FIG. 5 is a sectional view of other embodiment of an IC tag of the ovum preservation container inserted the inlet shown in FIG. 3.

Other embodiment of the IC tag 19 adopted an inlet 15, as shown in FIG. 5, comprises a thin-walled pipe 14 made of synthetic resin material, an inlet 15 inserted in the thin-walled pipe 14 and synthetic resin 20 molded in a body including the inlet 15.

An air hole 20a is formed in the molding in a body with inlet 15, and nitrogen gas N2 can be discharged from the air hole 20a.

As synthetic resin 20, non-electric conductive material such as synthetic resin material such as polypropylene, polyethylene and the like and elastic material such as silicon rubber, teflon [registered trademark of Kemars Co. Ltd.] rubber and the like can be adopted.

Figure 6:
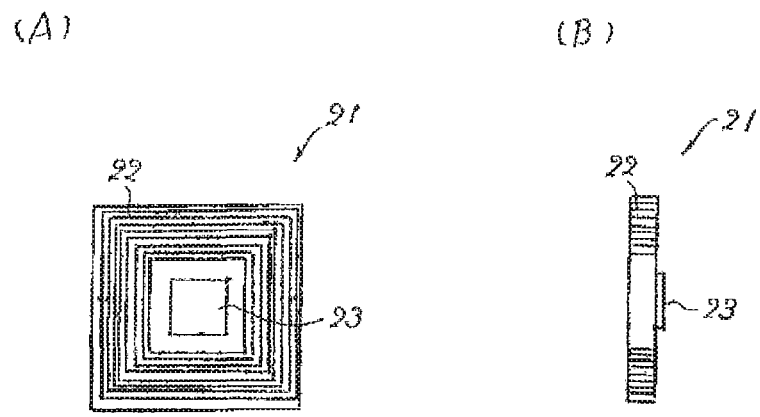
FIG. 6 (A) is a front view and (B) is a sectional view of other embodiment of an Inlet of an IC tag.

Further, as the inlet 21, as shown in FIG. 6, an inlet in which IC chip 23 is arranged inside the coil wound in plural layers to be a flat plate.

Here, instead of the inlet of wound-wire coil type, an inlet of base plate type in which IC chip is mounted on a coil base plate in which plural base plates formed coil pattern are piled to be a laminated structure may be adopted.

Figure 7:
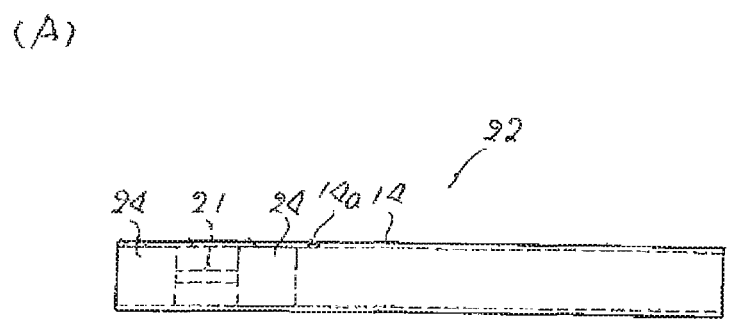
FIG. 7(A) is a sectional view and (B) is an exploded view of one embodiment of an IC tag of the ovum preservation container inserted the inlet shown in FIG. 6.
Figure 7:
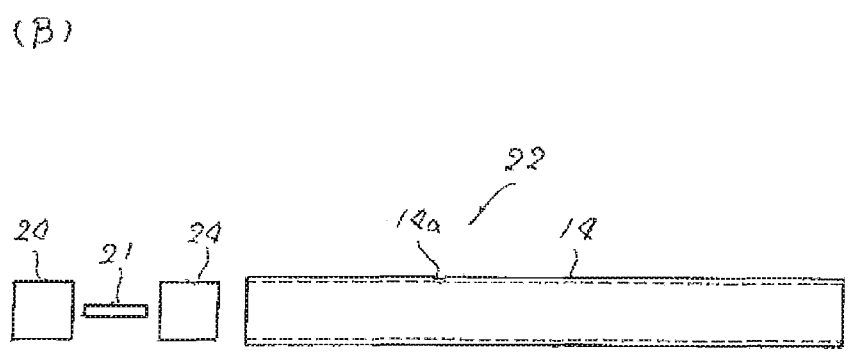

One embodiment of the IC tag 22 adopted an inlet 21, as shown in FIG. 7, comprises a thin-walled pipe 14 made of synthetic resin material, an inlet 21 inserted in the thin-walled pipe 14 and fixing members 24, 24 which fix the inlet 21 from both sides.

The fixing members 24 is formed by shaping non-electric conductive material such as synthetic resin, rubber, and the like, and synthetic resin material such as polypropylene, polyethylene and the like and elastic material such as silicon rubber, teflon [registered trademark of Kemars Co. Ltd.] rubber and the like can be adopted.

Further, an air hole 14a is formed on the peripheral surface of the thin-walled pipe 14, and nitrogen gas N2 can be discharged from the air hole 14a.

Figure 8:
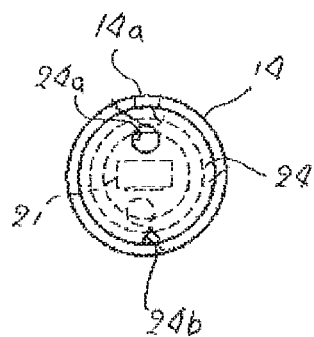
FIG. 8 is a sectional view of an IC tag of the ovum preservation container shown in FIG. 7.

Here, instead of forming an air hole 14a on the peripheral surface of the thin-walled pipe 14, as shown in FIG. 8, an air hole 24a or an air groove 24b may be formed in the fixing members 24, and thereby, similar operation and effect can be executed.

Figure 11:
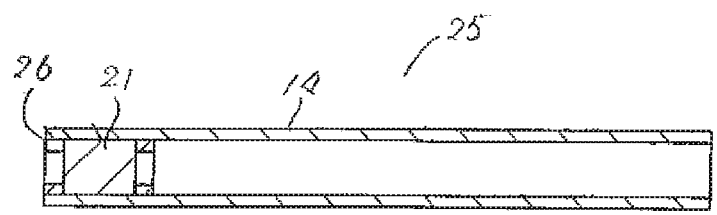
FIG. 11 is a sectional view of other embodiment of an IC tag of the ovum preservation container inserted the inlet shown in FIG. 6.

Other embodiment of the IC tag 25 adopted an inlet 21, as shown in FIG. 11, comprises a thin-walled pipe 14 made of synthetic resin material, a support member 26 inserted in the thin-walled pipe 14 and an inlet 21 supported by the support member 26.

Figure 9:
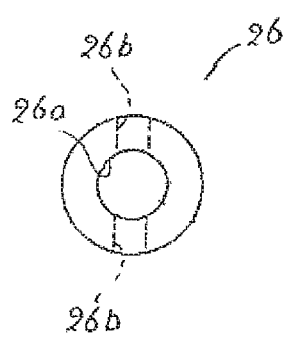
FIG. 9 (A) is a perspective view, (B) is a plan view, (C) is a front view and (D) is a sectional view of the holding member which holds the inlet shown in FIG. 6.
Figure 9:
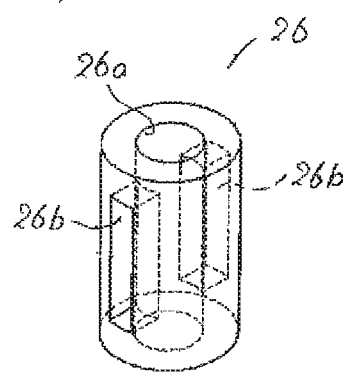
Figure 9:
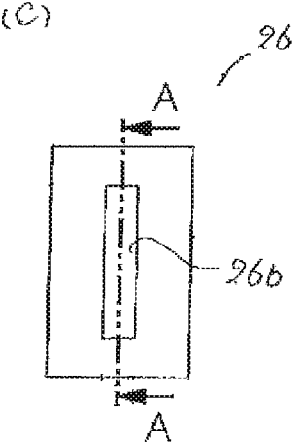
Figure 9:
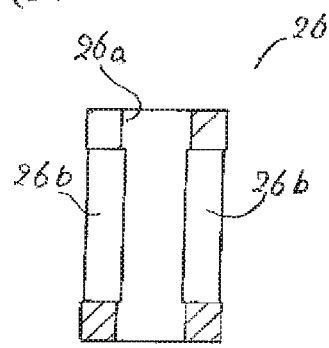

As shown in FIG. 9, the support member 26 is formed in cylindrical shape using synthetic resin, and a penetrated hole 26a is formed in axis direction and slits 26b, 26b penetrated in diameter direction are formed.

Figure 10:
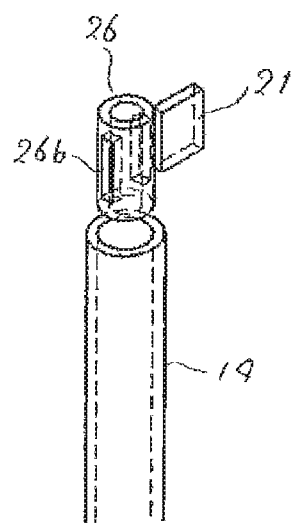
FIG. 10 is a perspective view showing a method of comprising the IC tag of the ovum preservation container inserted the inlet shown in FIG. 6.

As shown in FIG. 10, the inlet 21 is inserted the slits 26b, 26b of the support member 26 and is fixed and supported in the support member 26. And then, by inserting the support member 26 into the thin-walled pipe 14, as shown in FIG. 11, IC tag 25 is configured.

As for the support member 26, non-electric conductive material such as synthetic resin, rubber and the like, and synthetic resin material such as polypropylene, polyethylene and the like and elastic material such as silicon rubber, teflon [registered trademark of Kemars Co. Ltd.] rubber and the like can be adopted.

Figure 12:
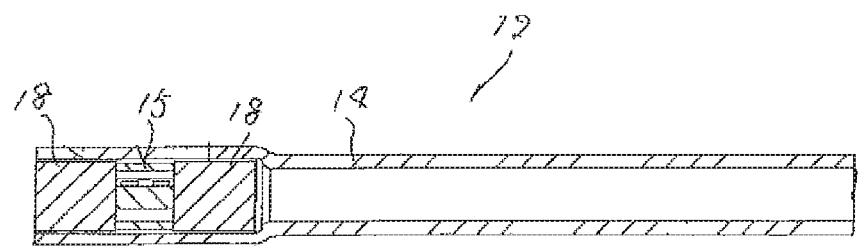
FIG. 12 is a sectional view of other embodiment of an IC tag of the ovum preservation container inserted the inlet shown in FIG. 3.
Figure 13:
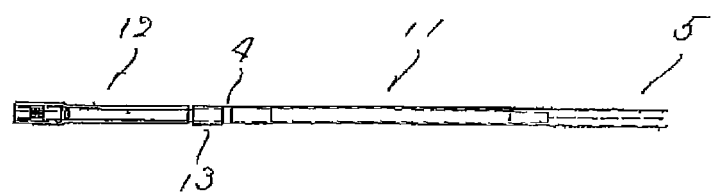
FIG. 13 is a front view of other embodiment of the ovum preservation container inserted the inlet shown in FIG. 6.

In case that the thin-walled pipe 14 is formed by material having elasticity, even if an external diameter of the fixing member 18 is a little larger than an internal diameter of the thin-walled pipe 14, as shown in FIGS. 12 and 13, the fixing member 18 can be pressed and inserted into the thin-walled pipe 14.

As the result, the fixing member 18 is pressed strongly by the thin-walled pipe 14 and the inlet 15 cannot get out easily.

Further, even if an internal diameter of the thin-walled pipe 14 of IC tag is a little smaller than an external diameter of the rear end portion of the rod-like portion of the ovum preservation container 1, as shown in FIG. 13, he thin-walled pipe 14 can be mounted in expanding the thin-walled pipe 14.

Figure 14:
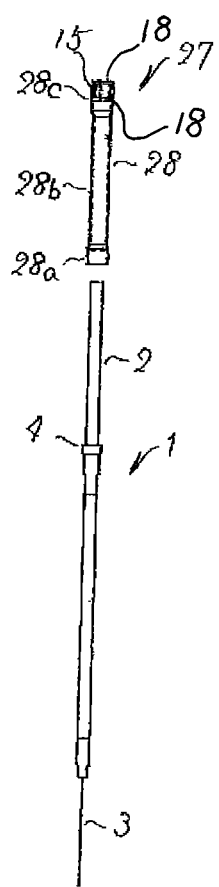
FIG. 14 is a front view of other embodiment of the ovum preservation container inserted the inlet shown in FIG. 6.

Other embodiment of the IC tag 27 adopted an inlet 15, as shown in FIG. 14, comprises a thin-walled pipe 28 made of synthetic resin material, an inlet 15 inserted in the thin-walled pipe 28 and fixing members 18, 18 which fix the inlet 15 from both sides.

And then, as shown in FIG. 14, an internal diameter of an opening portion 28a and a closing potion 28c of the thin-walled pipe 28 is almost equal to a diameter of a circle of the rod-like portion 2 of the ovum preservation container 1, and an internal diameter of the middle portion 28a is a little smaller than a diameter of the circle of the rod-like portion.

As the IC tag 27 is configured as mentioned above, it is easy to insert the IC tag 27 into the rod-like portion 2 of the ovum preservation container 1, and by pressing into the rod-like portion 2, the rod-like portion 2 is pressed by the middle portion 28b and IC tag 27 can be fixed strongly to the rod-like portion 2.

Here, the rod-like portion 2 of the ovum preservation container 1 is configured in a square pillar shape, by pressing the thin-walled pipe 28 in the rod-like portion 2, the thin-walled pipe 28 is transformed imitating the cross section of a square pillar shape.

Although the thin-walled pipe 28 is formed using material of relatively low elasticity, the cross section of the thin-walled pipe 28 is transformed from a cylindrical shape to a square pillar shape and it is possible to insert the rod-like portion 2 to the thin-walled pipe 28. Then a restoration force acts as a tightening force and IC tag 27 is fixed securely to the rod-like portion 2.

Figure 15:
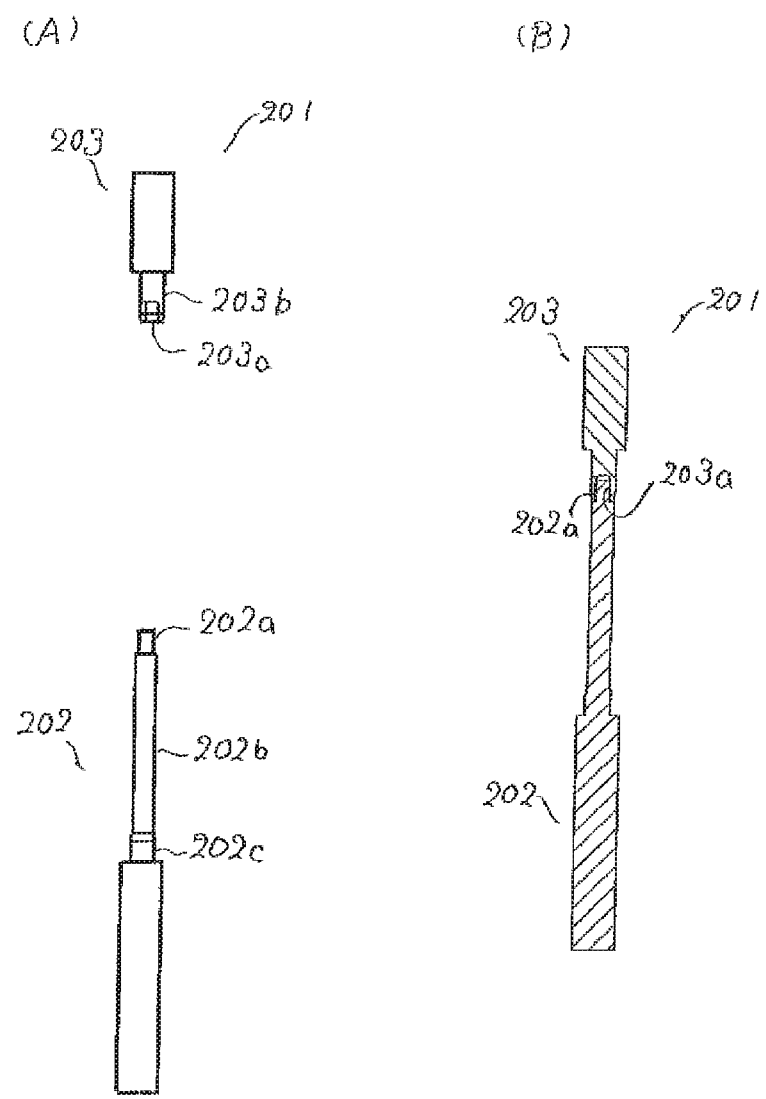
FIG. 15 (A) is a front view of a state of separating of a formation jig forming a thin-walled pipe comprising an IC tag shown in FIG. 14 and (B) is a longitudinal sectional view of a state of fitting together.

Such a thin-walled pipe 28 can be formed using a formation jig 201 as shown in FIG. 15.

As a material of the thin-walled pipe 28, a material having heat contractility is used.

As shown in FIG. 15, the formation jig 201 comprises a jig body 202 and a jig head 203, and a tip projection portion 202a of the jig body 202 is inserted into a fitting hole portion 203a of the jig head 203 to be fitted together.

And an external diameter of a middle rod portion 202b of the jig body 202 is a little smaller than an external diameter of a circumscribed circle the rod-like portion 62 of the ovum preservation container 61, an external diameter of a basic rod portion is almost equal to an external diameter of a circumscribed circle of the rod-like portion 2 of the ovum preservation container 1.

Further, an external diameter of a tip rod portion 203b of the jig head 203 is almost equal to an external diameter of a circumscribed circle of the rod-like portion 2 of the ovum preservation container 1.

Figure 16:
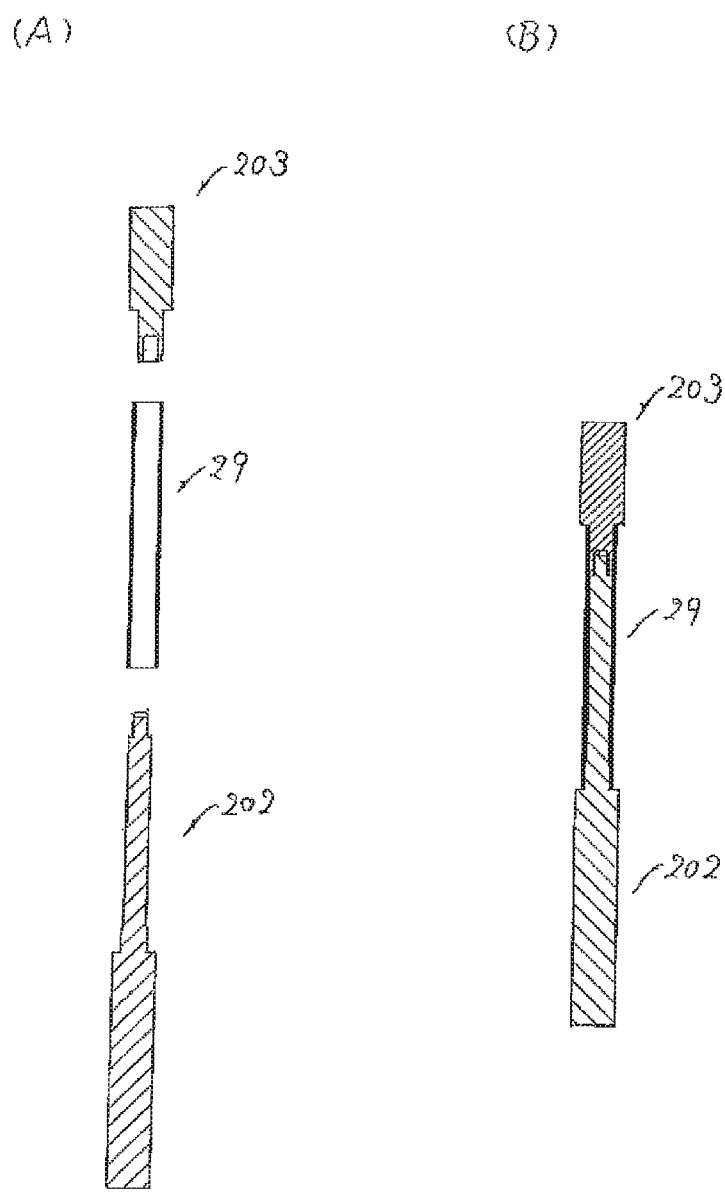
FIG. 16(A) is an exploded view and (B) is a sectional view showing a method of forming the thin-walled pipe comprising the IC tag shown in FIG. 14.

First, as shown in FIG. 16 (A), a raw pipe 29 an external diameter of which is almost equal to an external diameter of a circumscribed circle of the rod-like portion 2 of the ovum preservation container 1 is inserted to the base rod portion 202c of the jig body 202, and then, as shown in FIG. 16 (B), the tip rod portion 203b of the jig head 203 is inserted from an end opening of the raw pipe 29 and the fitting hole 203a is fitted on the tip project portion 202a.

Figure 17:
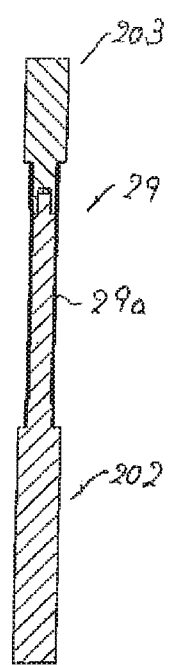
FIG. 17(A) is a sectional view and (B) is an exploded view showing a method of forming the thin-walled pipe comprising the IC tag shown in FIG. 14.
Figure 17:
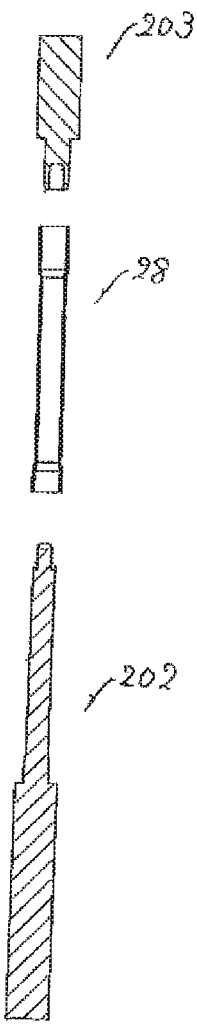

Next, by adding heat of predetermined temperature to the raw pipe 29, as shown in FIG. 17 (A), a middle portion 67a of the raw pipe 29 is contracted and is formed as a shape of the formation jig 201. And then, by separating the jig body 202 from the jig head 203, as shown in FIG. 17 (B), the thin-walled pipe 28 a middle portion 28a of which has a small diameter can be formed.

As a method in which IC tag 12 is connected to the rear end portion of the rod-like part of the ovum preservation 1, any method without fitting in may be adopted.

Figure 18:
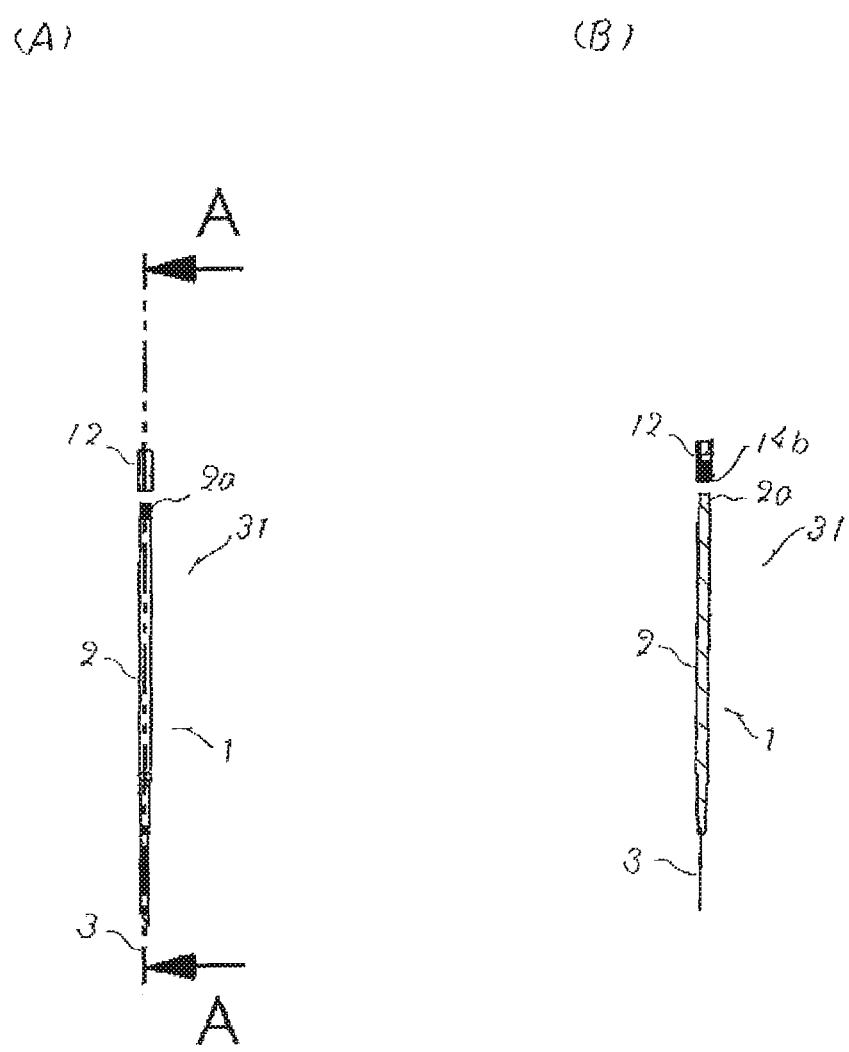
FIG. 18 (A) is a front view and (B) is an exploded view of other embodiment of an ovum preservation container of the present invention.

For example, as shown in FIG. 18, a male screw portion 2a may be formed in the rear end portion of the rod-like part 2 of the ovum preservation container 1, and a female screw portion 14a may be formed in the opening portion of the thin-walled pipe 14 of IC tag 12.

Owing to such a structure, by screwing a male screw portion 2a of the rod-like part 2 in a female screw portion 14a of IC tag 12 and rotating the IC tag 12 to be tightened, the ovum preservation container 31 mounted IC tag 12 can be easily configured.

Figure 19:
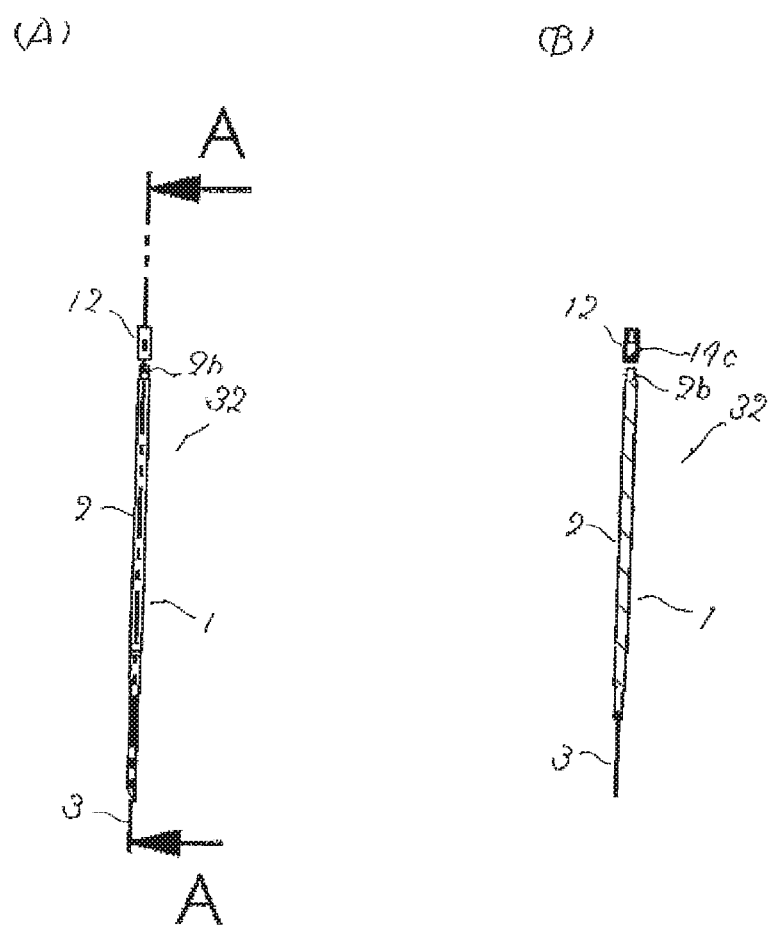
FIG. 19 (A) is a front view and (B) is an exploded view of other embodiment of an ovum preservation container of the present invention.
Figure 20:
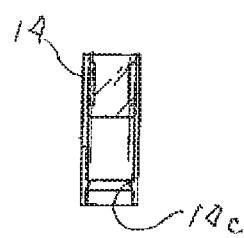
FIG. 20 is a sectional view of a main part of the ovum preservation container shown in FIG. 19.
Figure 20:
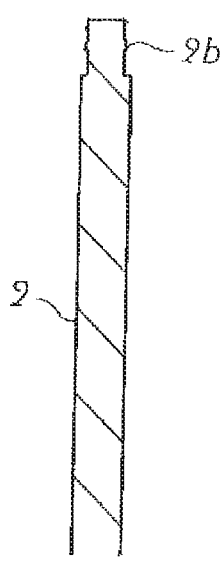

Further, as shown in FIGS. 19 and 20, a projection portion 2b may be formed in the rear end portion of the rod-like part 2 of the ovum preservation container 1, and a projection portion 14c may be formed in the opening portion of the thin-walled pipe 14 of IC tag 12.

Owing to such a structure, by inserting the opening portion of IC tag 12 into the rear end portion of rod-like part 2, and pressing the projection portion 14c over a projection portion 2b, the ovum preservation container 32 mounted IC tag 12 can be easily configured.

As the other embodiment, instead of inserting IC tag, IC tag may be included to the ovum preservation container so as to be structured in a body.

Figure 21:
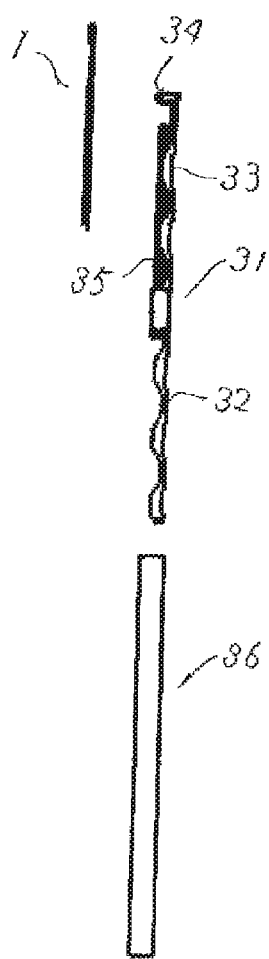
FIG. 21 is a front view of a conventional cane.

Conventional cane 31, as shown in FIG. 21, comprises a rod part 32, a support part 33 and a grasping part 34.

And a specimen tube 35 taken off a cap is fitted on and is supported on the supporting part 33, and plural ovum preservation container 1 are inserted and storage in the specimen tube 35.

Further, a sleeve 36 is covered on the cane 31 to protect the ovum preservation containers 1 and the specimen tubes 35.

Further, individual management was executed by attaching the labels variously colored to be distinguished to the rod part 32 and writing the necessary information on the surface of the labels with hand.

A cane 41 of the invention is configured by inserting IC tag 42 to the grasping part 34 to be mounted.

Figure 22:
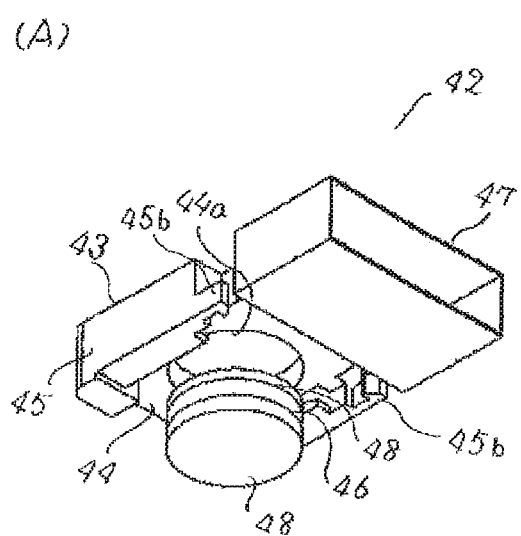
FIG. 22 (A) is a bottom perspective view and (B) is a top perspective view of an IC tag mounted on the cane shown in FIG. 21.
Figure 22:
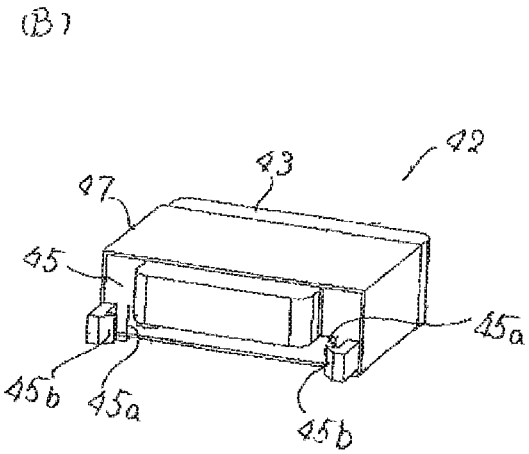

As shown in FIG. 22 (A), the IC tag 42 of the invention comprises a tag case 43 formed a flat portion 44 and a flame portion 45, a flex IC tag 46 fitted in the flat portion 44, and label 47 wound around the tag case 43.

A fitting hole 44*a* is formed in the flat portion 44, the flex IC tag 46 is fitted in the fitting hole 44*a*, and binder 48, 48 is applied from the both side of the flex IC tag 46 so that the fitting hole 44*a* buried is equal to other part of the flat portion 44.

As shown in FIG. 22 (B), an insert groove 45*a* is formed in the flame portion 45 of the tag case 43, connecting claws 45*b*, 45*b* are formed both side of the insert groove 45*a*.

And then, a latch structure is configured by the insert groove 45*a* and the connecting claws 45*b*, 45*b*.

Figure 23:
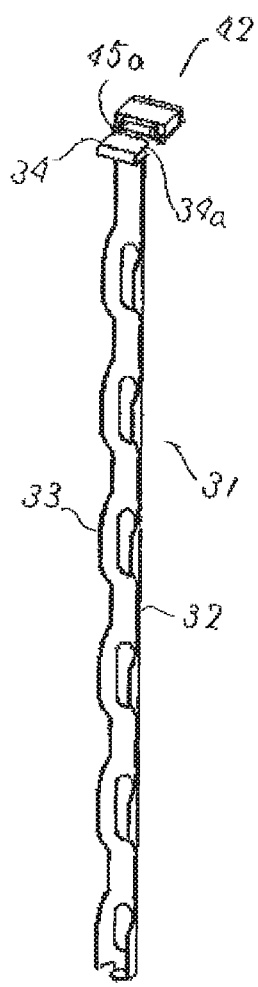
FIG. 23 is a perspective view showing the method of mounting an IC tag on the cane shown in FIG. 21.
Figure 24:
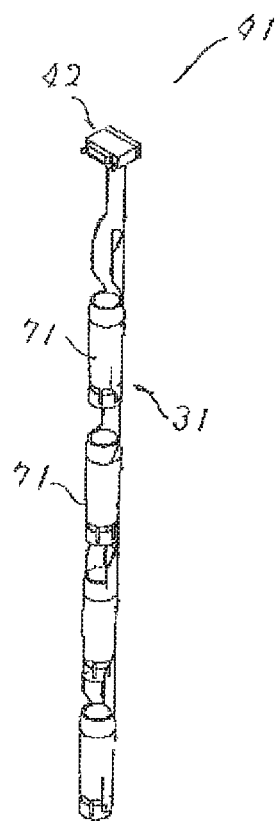
FIG. 24 is a perspective view of a cane of the present invention.

As shown in FIG. 23, by inserting the plate portion 34*a* of grasping portion 34 of the cane 31 to the groove portion 45*a* of the flame portion 45 of the IC tag 42, as shown in FIG. 24, a cane 41 mounted IC tag 42 can be configured.

Here, in case that the plate portion 34*a* is inserted to the inserting groove 45*a* of the IC tag 42 and the plate portion 34*a* is pressed in over the connecting claws 45*b*, 45*b*, the plate portion 34*a* is latched by the connecting claws 45*b*, 45*b*. Therefore, the IC tag 42 is not easily left out from the plate portion 34*a*.

As the same as mentioned above, ID is printed, or a label printed ID is attached on the surface of the IC tag 42 of the cane 31.

Accordingly, in case that information of the IC tag cannot be read by breakdown and so on, or IC tag is exchanged, information of IC tag can be restored and transferred.

Conventional canister 51 comprises a cylindrical portion 51*a*, a rod portion 51*b* and a hanging portion 51*c*.

Figure 25:
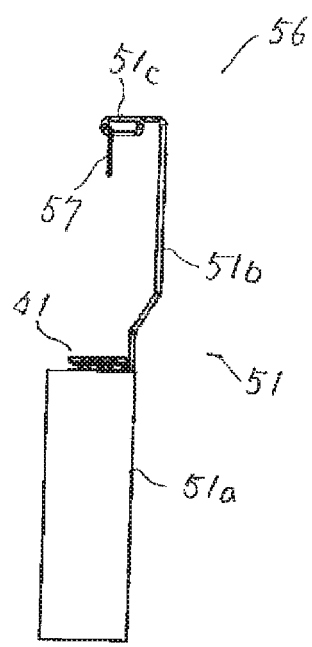
FIG. 25 is a front view of a canister of the present invention.
Figure 26:
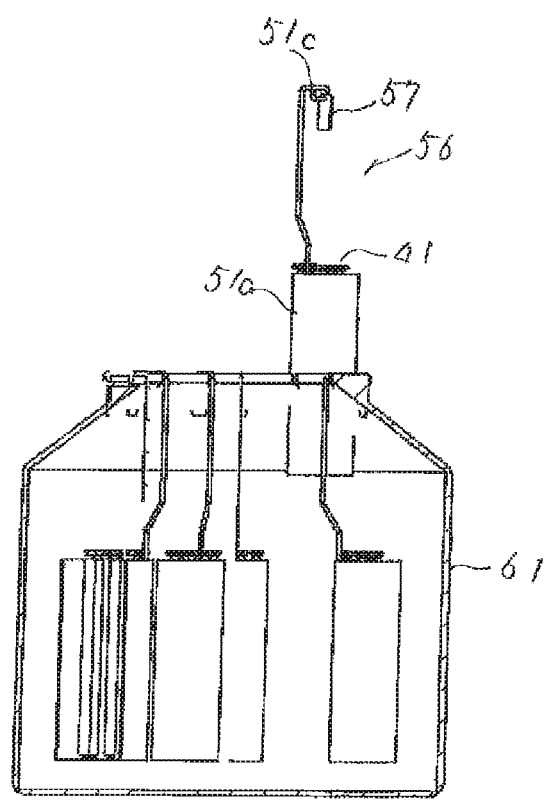
FIG. 26 is a front view showing the state of cryopreserving sperms, ovum, fertilized eggs and the like by inserting multiple canisters.

As shown in FIG. 25, a canister 56 of the invention is configured by hanging down the IC tag 57 in the hanging portion 51*c* of the canister 51. As shown in FIG. 25, plural cane 41, 41 are inserted within the cylindrical portion 51*a* of the canister 56 and, as shown in FIG. 26, the hanging portion 51*c* is hanged in the inner lid of the cryopreservation tank 61, and then the canisters 56 can be suspended within the cryopreservation tank 61.

Here, a cryopreservation tank number, a canister number, information of upper or lower position of canister and the like are recorded in the IC tag 57.

Conventionally, as sperm preservation containers, a specimen tube, a sperm preservation straw and the like are known.

Conventional specimen tube 71 comprises a tube body 72 and a cap 73 mounted and screwed on the tube body 72.

Figure 27:
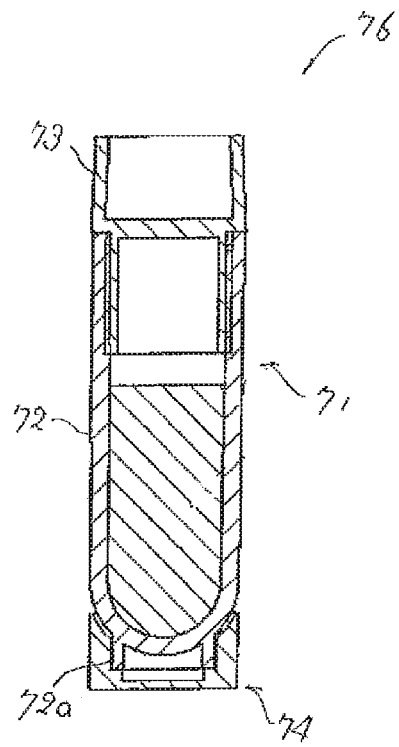
FIG. 27 is a sectional view of a specimen tube of the present invention.

As shown in FIG. 27, a specimen tube 76 of the invention is configured by mounting the IC tag 74 in the leg part 72*a* of the tube body 72.

And as shown in FIG. 24, plural specimen tubes 71, are fitted on the cane 41 and are stored.

Figure 28:
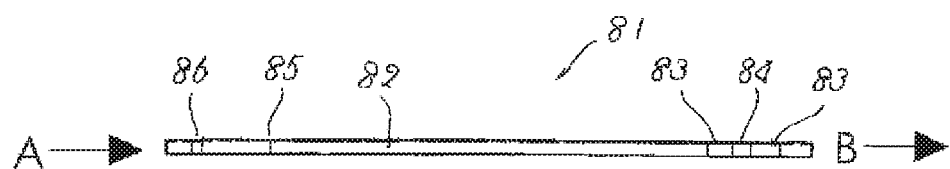
FIG. 28 is a front view of a conventional sperm preservation straw.

And as shown in FIG. 28, conventional sperm preservation straw 81 comprises a thin-walled pipe 82 made of synthetic resin, cotton stoppers 83, 83 inserted in one end portion of the thin-walled pipe 82, absorption member 84 inserted in between the cotton stoppers 83.

And sperms are injected into the thin-walled pipe 82 from the end A absorbing air from the end B of the thin-walled pipe 82, and the injection is stopped when the surface of liquid is reached at line 85.

And then, thermo-compression bonding or ultra-sonic pressing is executed in the other end of the thin-walled pipe 82, and sealing portion is formed to seal the thin-walled pipe 82.

Figure 29:
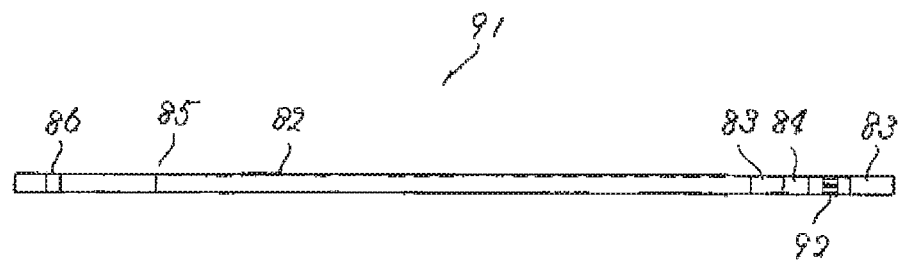
FIG. 29 is a front view of one embodiment of a sperm preservation straw of the present invention.

As shown in FIG. 29, a sperm preservation straw 91 of the invention is configured by including IC tag 92 in the outside cotton stopper 83 which is a component of the sperm preservation straw 81.

By including IC tag 92 in the outside cotton stopper 83, IC tag 92 can be supported without preventing the air ventilator.

Figure 30:
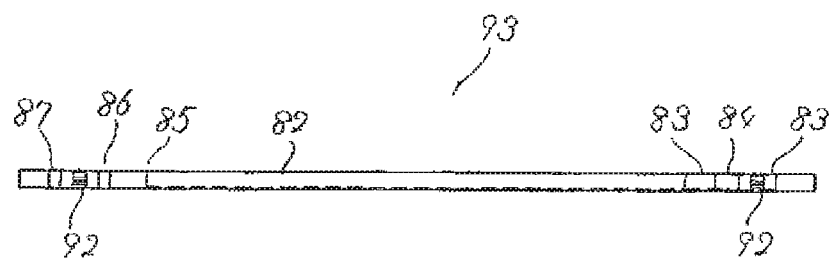
FIG. 30 is a front view of other embodiment of a sperm preservation straw of the present invention.

As shown in FIG. 30, a sperm preservation straw 93 may be configured by inserting the IC tag 92 outside the sealing portion 86 of the sperm preservation straw 91, executing thermo-compression bonding or ultra-sonic pressing in the outside to form a sealing portion 87.

In the sperm preservation straw 93, the other configuration is the same as that of the sperm preservation straw 91. Therefore, the same component members are shown by the same signs.

Now, from the point of view of sanitation, it is preferable to use the IC tags as mentioned above which are sterilized by radial rays, autoclave, plasma, gas and so on.

Figure 31:
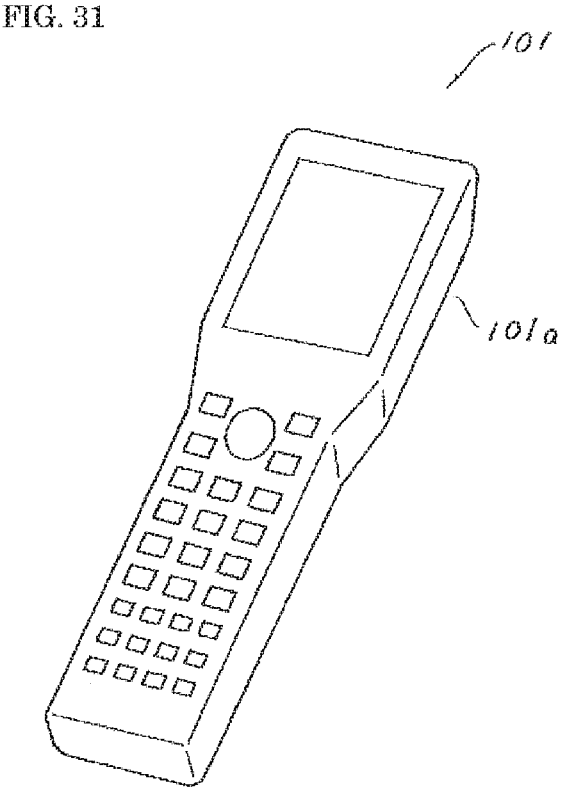
FIG. 31 is a perspective view of an identification code/IC tag reader.

In the storage room, an embryo cultivator in working time carries an identification code/IC tag reader 101 as shown in FIG. 31.

When the cryopreservation of fertilized eggs or sperms is started, the cryopreservation state is recognized, the melting work is executed, the cryopreservation is finished (abolition) and the like, the embryo cultivator puts the antenna 101*a* of the identification code/IC tag reader 101 close to the IC tag 57, 42, 12, 92 which are mounted on the cryopreservation tank 61, the canister 56, the cane 41, the ovum preservation container 11, and the sperm preservation straw 91 and reads ID, a patient information and preservation information which are stored in the IC tag 57, 42, 12, 92.

Here, it is easy to read the IC tag 57, 42 mounted on the canister 56, cane 41 by putting the identification code/IC tag reader 101 close to the IC tag 57, 42, because the IC tag 57, 42 has a large external diameter relatively. However, it is feared not to read the IC tag 12, 92 mounted on the ovum preservation container 11, the sperm preservation straw 91 by putting the identification code/IC tag reader 101 close to the IC tag 12, 92, because the IC tag 12, 92 has a minute external diameter.

Further, the antenna 101*a* of the identification code/IC tag reader 101 is arranged in the front side or in the back side of the identification code/IC tag reader 101 and it is necessary to read in the state corresponding the IC tag 12, 92 with the location of the antenna 101*a*, and therefore, the reading work takes a long time.

Therefore, in the invention, an extended antenna 111 capable of working in liquid nitrogen can be attached to the identification code/IC tag reader 101.

Figure 32:
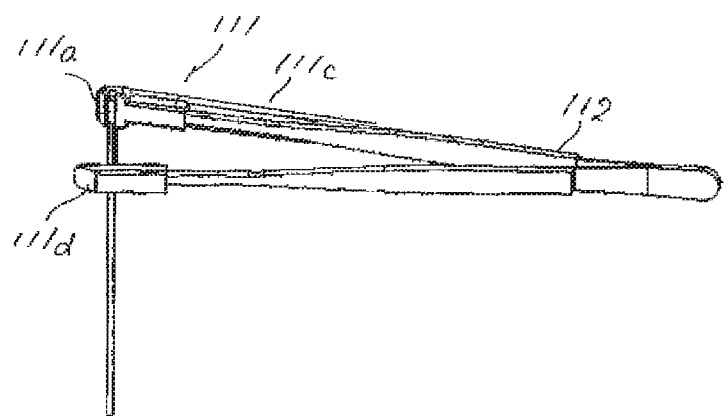
FIG. 32 (A) is a usage state view and (B) is an enlarged view of main part of one embodiment of an extended antenna attached to the identification code/IC tag reader shown in FIG. 31.
Figure 32:
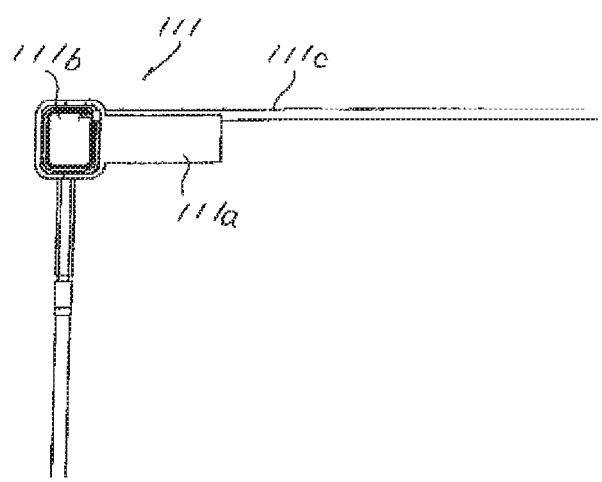
Figure 33:
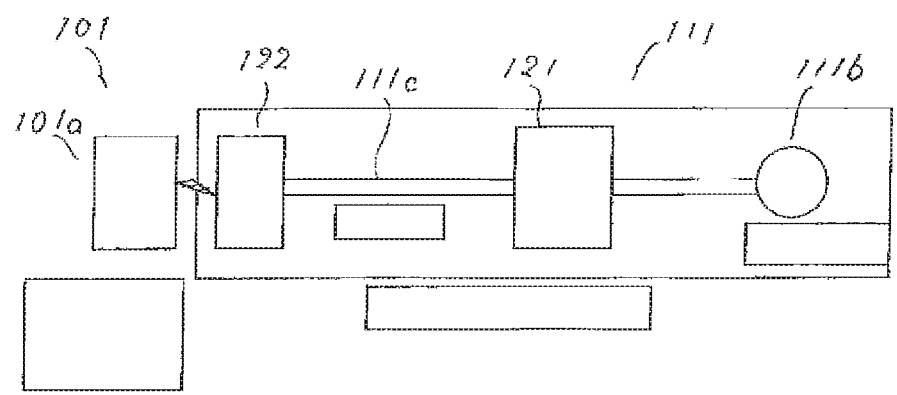
FIG. 33 is a diagram of the extended antenna shown in FIG. 32.

As shown in FIGS. 32 and 33, the extended antenna 111 comprises a holding member 111a, an antenna element 111b, a connecting cable 111c and a nipping member 111d.

As shown in FIG. 33, a matching circuit 121 for matching to a resonant circuit is formed in the antenna element 111b. The matching circuit 121 is configured by a circuit to match the resonant circuit of 13.5 MHz frequency and to match the impedance of the extended antenna to 50Ω in order to efficiently read a high frequency electric current of 13.56 MHz which is sent from the identification code/IC tag reader 101 and transmitted to antenna element 111b.

Further, as shown in FIG. 33, in an adapter connected to the identification code/IC tag reader 101, a coil for transmitting energy and signal by mutual electromagnetic induction is arranged against an attachment metal fitting and an antenna 101a of the identification code/IC tag reader 101.

As for the holding member 111a, a fitting groove is formed in the tip end portion of the holding member 111a to fit in and sustain the IC tag 12 for ovum preservation container 11 and a fitting hole is formed in the rear end portion of the holding member 111a to fit in and insert a tip portion of a sustaining tool such as a pair of tweezers 112 and the like.

The antenna element 111b is fitted in the inner side of the tip end portion of the sustaining member 111a and the connection cable 111c is extended out from the one end portion of the antenna element 111b.

As for the nipping member 111d, a fitting hole is formed in the rear end portion of the nipping member 111d to fit in and insert a tip portion of a sustaining tool such as a pair of tweezers 112 and the like.

As shown in FIG. 32 (A), the both tip portions of tweezers 112 are fitted in the fitting hole of the holding member 111a and the fitting hole of the nipping member 111d and the IC tag 12 of the ovum preservation container 11 is fitted in the fitting groove of the holding member 111a.

And then, by closing the tip portions of the pair of tweezers 112 and nipping the IC tag 12 between the holding member 111a and the nipping member 111d, the antenna element 111b can be received electromagnetic energy from IC tag 12.

The electromagnetic energy is transmitted to the antenna 101a of the identification code/IC tag reader 101 via the connecting cable 111c. Therefore, information data stored in IC tag 12 can be read by the identification code/IC tag reader 101.

Figure 34:
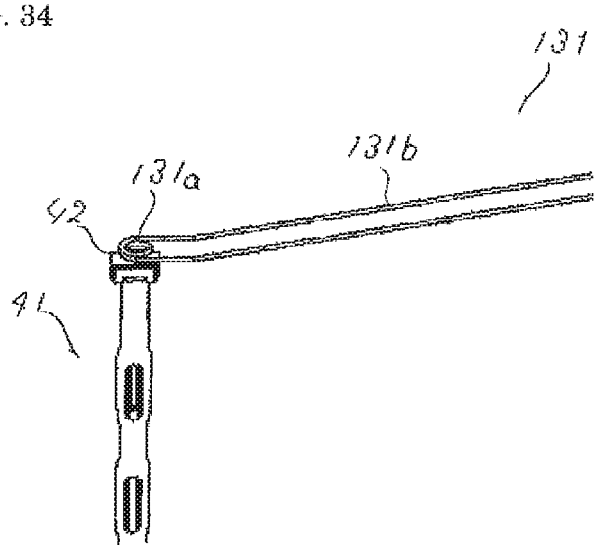
FIG. 34 is a usage state view of other embodiment of the extended antenna attached to the identification code/IC tag reader shown in FIG. 31.

In order to read the IC tag 42 mounted on the cane 31, the extended antenna 131 as shown in FIG. 34 may be attached to the identification code/IC tag reader 101.

As shown in FIG. 34, the extended antenna 131 comprises an antenna element 131a and a connecting cable 131b.

Here, antenna element 131a is formed by material having a heat-resistance against −196° C. and a high stiffness. The connecting cable is also configured by material having a heat-resistance against −196° C.

Owing to the extended antenna 131, even if in the state that the cane 41 is sustained in the canister 56 which is suspended within the preservation tank 61, the IC tag 42 can be read by going the antenna element 131a close to the IC tag 42.

Further, antenna element 131a is small and does not have any obstacle such as a cover, and therefore, even if plural IC tags 42 for cane 41 are arranged closely, predetermined IC tag 42 can be read easily.

As mentioned above, information stored in the IC tag is transmitted to the server installed in the office via intra-facility network and is stored in the server. A person in charge, a doctor, an embryo cultivator and the like can recognize patient information, ova information, preservation information in appropriate time by using a personal computer installed in the office and a personal computer installed in the examination room and receiving information from the server.

On the other hand, since the server is connected to intra-facility network and is also connected to the cloud server via Internet, a patient can require information on himself by using his own portable information terminal device and accessing the cloud server.

In the present invention, IC tags stored ID, specimen number, patient name, collecting day and time and the like are attached to sperm preservation container, ovum preservation container, cane and the like, and thereby, an embryo cultivator can read the information by an identification code/IC tag reader. Therefore, the confusion of specimens to be the subject of treatment does not occur by mistaking a specimen number and the like.

Further, in the case that a sperm preservation container, an ovum preservation container, a cane and the like are taken out from a cryopreservation tank, even if frost and the like are attached to the surface of them, information can be read by an identification code/IC tag reader. Therefore, ID, a specimen number and the like can be recognized without removing frost and the like, and working efficiency of the embryo cultivator can be greatly improved.

It takes a little time to take out a sperm preservation container, an ovum preservation container, a cane and the like from the cryopreservation tank and recognize ID, a specimen number and the like by the embryo cultivator, or else, it is not necessary to take out them from liquid nitrogen.

Therefore, sperms, ova, and the like does not change in quality rarely in the working time, after all, the fertilization ratio and the implantation ratio can be improved greatly.

Further, invention, in the case that an embryo cultivator executes work of collection, treatment, fertilization, cultivation, preservation, implantation and the like of ova and sperms, he enters the information in the recording display of a personal computer and stores the information in the personal computer. Therefore, a patient can recognize the information in appropriate time by a portable phone and the like and thereby reliability of treatment can be improved.

As a result mentioned above, processing ability and working ability of an embryo cultivator become clear, effectivity of cultivation liquid depended on individual variation of fertilized eggs also become clear, and then, by improving the matter, pregnancy rate of infertility treatment can be expected to improve greatly.

Further, the cryopreservation container of the invention is described in the case adopted to the facility in which an in-vitro fertilization is executed, the invention can be adopted to the case in which cryopreservation or in-vitro fertilization of sperms, ova, and the like of animals such as a cow, a horse and the like is executed, without human case.

REFERENCE SIGNS LIST

1 Ovum preservation container
2 Rod-like portion
11 Ovum Preservation container
12 IC tag
14 Thin-walled pipe
15 Inlet 18 Fixing members
20 Synthetic resin
31 Cane
34 Grasping part
41 Cane
42 IC tag
43 Tag case
45a Insert groove
45b Connecting claws
47 Label
46 Flex IC tag
51 Canister
51c Hanging portion
56 Canister
57 IC tag
71 Specimen tube
72a Leg part
74 IC tag
76 Specimen tube
81 Sperm preservation straw
83 Cotton stopper
86 Sealing portion
87 Sealing portion
91 Sperm preservation straw
92 IC tag

The invention claimed is:

1. A cryopreservation system to cryopreserve reproductive cells, the cryopreservation system including a cryopreservation tank, a canister, a cane, and a cryopreservation container, wherein the cryopreservation container is selected from the group consisting of an ovum preservation container and a sperm preservation container,
wherein an integral circuit (IC) tag is mounted at least on the canister, the cane, or the cryopreservation container, and an identification (ID) code connected to an individual ID number of the IC tag recorded in the IC tag is printed on a surface of the IC tag or printed on a label attached to the surface of the IC tag, wherein the IC tag includes a color for individual identification painted thereon,
a type code configured to identify a type of cryopreservation container, ID number and color information for individual identification are recorded in the IC tag, and
wherein the IC tag is configured to operate under liquid nitrogen environment of −196° Centigrade (C) by at least increasing a Q (Quality Factor) value via reduction of series resistance (R) in a series resonant circuit, thereby increasing energy transmission and communication efficiency and by isolating a coil of the IC tag in a manner that the coil does not contact the liquid nitrogen used for cryopreservation directly.

2. The cryopreservation system according to claim 1, wherein the cryopreservation container is the ovum preservation container, wherein the ovum preservation container comprises a rod-like portion having a square pillar, a support plate made of synthetic resin and a guard portion formed in the middle portion of the rod-like portion,
the IC tag formed by providing an inlet inside a thin-walled pipe made of a synthetic resin that is fitted from the rear end of the rod-like portion of the ovum preservation container.

3. The cryopreservation system according to claim 2, wherein the inlet is integrally molded with a nonconductive synthetic resin material.

4. The cryopreservation system according to claim 1, wherein the cryopreservation container is the ovum preservation container, wherein the ovum preservation container comprises a rod-like portion having a square pillar, a support plate made of synthetic resin and a guard portion formed in the middle portion of the rod-like portion,
the IC tag formed by providing an inlet inside a thin-walled pipe made of a synthetic resin that is screwed or engaged with the rear end of the rod-like portion of the ovum preservation container.

5. The cryopreservation system according to claim 4, wherein an internal diameter of a middle part of the thin-walled pipe of the IC tag is a little smaller than a diameter of a circumscribed circle in the rod-like portion of the ovum preservation container.

6. The cryopreservation system according to claim 4, wherein the ID code is connected to aft the ID number recorded in the IC tag that is printed on the surface of the rod-like portion of the ovum preservation container or the label on which the ID code is printed is attached to the surface of the rod-like portion of the ovum preservation container.

7. The cryopreservation system according to claim 4, wherein the color for individual identification is painted on the surface of the rod-like portion of the ovum preservation container or is painted on the surface of the inlet of the ovum preservation container.

8. The cryopreservation system according to claim 4, wherein the inlet is fixed at both ends by means of fixing members composed of a nonconductive material.

9. The cryopreservation system according to claim 1, wherein the cryopreservation container is a sperm preservation container, wherein the sperm preservation container is a sperm preservation straw and the IC tag is included in a straw terminal end cotton stopper which is a component of the sperm preservation straw.

10. The cryopreservation system according to claim 1, wherein the cryopreservation container is the sperm preservation container, wherein the sperm preservation container is a sperm preservation straw and the IC tag is inserted outside of a sealing portion of the sperm preservation straw, and wherein the sealing portion is formed by thermo-compression bonding or ultra-sonic pressing around the outside of the sperm preservation straw.

11. The cryopreservation system according to claim 1, wherein the cryopreservation container is the sperm preservation container, wherein the sperm preservation container is a specimen tube and the IC tag is mounted in a leg portion of a body of the specimen tube.

12. The cryopreservation system according to claim 1, wherein the IC tag is inserted and mounted in a hooking portion of a body of the cane.

13. The cryopreservation system according to claim 12, wherein the IC tag is formed by providing a tag case forming a frame-like portion fitted to a flex IC tag.

14. The cryopreservation system according to claim 1, wherein the IC tag is suspended from a hooking portion of the canister.

15. The cryopreservation system according to claim 14, wherein a cryopreservation tank number and a canister number of the canister is registered in the IC tag.

16. The cryopreservation system according to claim 1, wherein the IC tag is sterilized by radiation, autoclave, plasma or gas.

* * * * *